United States Patent
Enomura et al.

(10) Patent No.: US 12,201,728 B2
(45) Date of Patent: *Jan. 21, 2025

(54) METHOD OF PRODUCING A MICROSPHERE COMPRISING PLGA OR PLA IN WHICH A BIOLOGICALLY ACTIVE SUBSTANCE IS UNIFORMLY DISPERSED

(71) Applicant: M. TECHNIQUE CO., LTD., Izumi (JP)

(72) Inventors: Masakazu Enomura, Izumi (JP); Kaeko Araki, Izumi (JP)

(73) Assignee: M. TECHNIQUE CO., LTD., Izumi (JP)

(*) Notice: Subject to any disclaimer, the term of this patent is extended or adjusted under 35 U.S.C. 154(b) by 399 days.

This patent is subject to a terminal disclaimer.

(21) Appl. No.: 17/673,429

(22) Filed: Feb. 16, 2022

(65) Prior Publication Data

US 2022/0168224 A1 Jun. 2, 2022

Related U.S. Application Data

(62) Division of application No. 17/259,690, filed as application No. PCT/JP2020/034524 on Sep. 11, 2020, now Pat. No. 11,285,109.

(30) Foreign Application Priority Data

May 8, 2020 (WO) .................. PCT/JP2020/018731

(51) Int. Cl.
*A61K 9/16* (2006.01)
(52) U.S. Cl.
CPC .................................. *A61K 9/1647* (2013.01)
(58) Field of Classification Search
CPC ....................................................... A61K 9/1647
See application file for complete search history.

(56) References Cited

U.S. PATENT DOCUMENTS 5,945,126 A 8/1999 Thanoo et al.
5,945,129 A 8/1999 Knerr et al.
(Continued)

FOREIGN PATENT DOCUMENTS

CN 103054809 A 4/2013
EP 0 442 671 B1 6/1995
(Continued)

OTHER PUBLICATIONS

Lee et al., PLA Micro- and Nano-Particles, Adv Drug Delivery Rev, 15; 107; 178-191 (Year: 2016).*

(Continued)

*Primary Examiner* — Carlos A Azpuru
(74) *Attorney, Agent, or Firm* — Birch, Stewart, Kolasch & Birch, LLP

(57) ABSTRACT

The present application provides a microsphere comprising a lactic acid-glycolic acid copolymer (PLGA) or polylactide (PLA) as a main component, in which a biologically active substance is uniformly dispersed, wherein an average volume-based particle diameter of the microsphere is 1 μm or more and 150 μm or less, and a variation coefficient of area ratios in six regions is 0.35 or less, wherein the area ratios in six regions are calculated by (s/A)×100 (%) wherein the six regions are prepared by preparing a cross section observation sample obtained by cutting the microsphere; observing the cross section observation sample with an electron microscope at a magnification capable of confirming the biologically active substance in the microsphere or a higher magnification; and dividing the electron microscope observation image into six regions; and A is an area of a respective divided region, and s is a sum of cross section areas of the biologically active substance included in the respective divided region. The microsphere of the present invention can appropriately control the initial release amount of the bio- (Continued)

logically active substance and its release rate during a subsequent release period, and can continuously release the biologically active substance in vivo for a predetermined period of time.

5 Claims, 8 Drawing Sheets

(56) References Cited

U.S. PATENT DOCUMENTS

| | | | |
|---|---|---|---|
| 8,222,301 | B2 | 7/2012 | Enomura |
| 9,211,510 | B2 | 12/2015 | Enomura |
| 11,285,109 | B2 * | 3/2022 | Enomura ............... A61K 31/57 |
| 11,617,720 | B2 | 4/2023 | Enomura et al. |
| 2006/0134223 | A1 | 6/2006 | Yamada |
| 2007/0059363 | A1 | 3/2007 | Lee et al. |
| 2008/0102131 | A1 | 5/2008 | Nagira et al. |
| 2009/0004283 | A1 | 1/2009 | Petersen et al. |
| 2009/0011355 | A1 | 1/2009 | Shibai |
| 2010/0155310 | A1 | 6/2010 | Enomura |
| 2010/0203151 | A1 | 8/2010 | Hiraoka |
| 2010/0272820 | A1 | 10/2010 | Lim et al. |
| 2014/0341997 | A1 | 11/2014 | Kim et al. |
| 2015/0321154 | A1 | 11/2015 | Enomura |
| 2016/0089335 | A1 | 3/2016 | Ohri et al. |
| 2017/0135960 | A1 | 5/2017 | Yu et al. |
| 2017/0281547 | A1 | 10/2017 | Karavas et al. |

FOREIGN PATENT DOCUMENTS

| | | |
|---|---|---|
| JP | 4-114725 A | 4/1992 |
| JP | 2653255 B2 | 9/1997 |
| JP | 2001-512461 A | 8/2001 |
| JP | 2002-534392 A | 10/2002 |
| JP | 2005-15476 A | 1/2005 |
| JP | 2005-35994 A | 2/2005 |
| JP | 2009-520727 A | 5/2009 |
| JP | 2009-132871 A | 6/2009 |
| JP | 2010-510206 A | 4/2010 |
| JP | 2010-531303 A | 9/2010 |
| JP | 2011-189348 A | 9/2011 |
| JP | 4856752 B2 | 1/2012 |
| JP | 5147091 B1 | 2/2013 |
| JP | 2014-224114 A | 12/2014 |
| JP | 2016-69378 A | 5/2016 |
| JP | 2017-509661 A | 4/2017 |
| WO | WO 00/40259 A1 | 7/2000 |
| WO | WO 01/10414 A1 | 2/2001 |
| WO | WO2008/053920 A1 | 5/2008 |
| WO | WO 2011/112576 A1 | 9/2011 |

OTHER PUBLICATIONS

Extended European Search Report dated Nov. 2, 2023 for Application No. 20934454.8.
Jordan et al., "Comparative Study of Chemoembolization Loadable Beads: In vitro Drug Release and Physical Properties of DC Bead and Hepasphere Loaded with Doxorubicin and Irinotecan", J Vasc Interv Radiol, vol. 21, No. 7, Jul. 2010, pp. 1084-1090.
International Search Report (PCT/ISA/210) issued in PCT/JP2020/034524 mailed on Oct. 27, 2020, with translation.
Lee et al., PLA Micro and Nano-Particles, Adv Drug Delivery Rev, 15; 107: 176-191 (Year: 2016).
Written Opinion (PCT/ISA/237) issued in PCT/JP2020/034524 mailed on Oct. 27, 2020, with translation.
U.S. Appl. No. 18/349,753, filed Jul. 10, 2023.
U.S. Appl. No. 18/112,747, filed Feb. 22, 2023.
Kiss et al., "The Influence of Process Parameters on the Properties of PLGA-Microparticles Produced by the Emulsion Extraction Method," AIChE Journal, vol. 59, No. 6, 2013 (published online Dec. 20, 2012), pp. 1868-1881.
U.S. Office Action for U.S. Appl. No. 18/349,753, dated Apr. 17, 2024.
Zhao et al., "Hierarchically porous composite microparticles from microfluidics for controllable drug delivery," Nanoscale, vol. 10, 2018, pp. 12595-12604.
Busatto et al., "Effect of Particle Size, Polydispersity and Polymer Degradation on Progesterone Release from PLGA Microparticles: Experimental and Mathematical Modeling", International Journal of Pharmaceutics, vol. 536, No. 1, Dec. 5, 2017, pp. 360-369.
Chinese Office Action and Search Report dated May 25, 2023 for Application No. 202080100595.1 with an English translation.
Chinese Office Action and Search Report for Chinese Application No. 202080025520.1, dated Aug. 12, 2022, with an English translation of the Chinese Office Action.
Dong et al., "Development of composite PLGA microspheres containing exenatide-encapsulated lecithin nanoparticles for sustained drug release", 2020, Elsevier, Asian Journal of Pharmaceutical Sciences, vol. 15, pp. 347-355, 2019.
Extended European Search Report for European Application No. 20934379.7, dated Mar. 23, 2023.
International Search Report, issued in PCT/JP2020/044366, dated Jan. 12, 2021, with English translation.
Kikuchi, Drug Delivery System, 2014, vol. 29, No. 1, pp. 51-63.
Product information for "PC-98T Egg yolk lecithin I 93685-90-6", retrieved from: <http://en.avt-avt.com/product-item-79.html> on Jul. 28, 2022, pp. 1-2.
Soppimath et al., "Biodegradable polymeric nanoparticles as drug delivery devices", 2001, Elsevier, Journal of Controlled Release, vol. 70, pp. 1-20.
The Merck Index Online (TM) entry for "Latanoprost" (M6701), p. 1, 2013.
The Merck Index Online entries for Camptothecin (M3007), Cyclosporines (M4020), Ibuprofen (M6189), Indomethacin (M6279), Tacrolimus (M 10425), Tranilast (M11001), and Triamcinolone (M11027), pp. 1-14, 2013.
Wang et al., "Enhanced encapsulation and bioavailability of breviscapine in PLGA microparticles by nanocrystal and water-soluble polymer template techniques", 2017, Elsevier, European Journal of Pharmaceutics and Biopharmaceutics, vol. 115, pp. 177-185.
Written Opinion of the International Searching Authority, issued in PCT/JP2020/044366, dated Jan. 12, 2021, with English translation.
Xie et al., "Progesterone PLGA/mPEG-PLGA Hybrid Nanoparticle Sustained-Release System by Intramuscular Injection", 2018, Springer, Pharmaceutical Research, vol. 35, No. 62, pp. 1-10.
Allison, "Analysis of initial burst in PLGA microparticles," Expert Opinion on Drug Delivery, vol. 5, No. 6, 2008, pp. 615-628.
U.S. Office Action for U.S. Appl. No. 18/349,753, dated Jul. 18, 2024.
Hewlings et al., "Curcumin: A Review of Its' Effects on Human Health," Foods, vol. 6, No. 92, 2017, pp. 1-11.
U.S. Office Action for U.S. Appl. No. 18/112,747, dated May 23, 2024.

* cited by examiner

METHOD OF PRODUCING A MICROSPHERE COMPRISING PLGA OR PLA IN WHICH A BIOLOGICALLY ACTIVE SUBSTANCE IS UNIFORMLY DISPERSED

CROSS-REFERENCE TO RELATED APPLICATIONS

This application is a Divisional of U.S. application Ser. No. 17/259,690, filed on Jan. 12, 2021, which is the National Phase under 35 U.S.C. § 371 of International Application No. PCT/JP2020/034524, filed on Sep. 11, 2020, which claims the benefit under 35 U.S.C. § 119(a) to National Phase Patent Application No. PCT/JP2020/018731, filed in Japan on May 8, 2020, all of which are hereby expressly incorporated by reference into the present application.

TECHNICAL FIELD

The present inventions relate to a microsphere in which a biologically active substance is uniformly dispersed and a sustained release formulation comprising the same. The present inventions specifically relate to a microsphere comprising a lactic acid-glycolic acid copolymer (PLGA) or polylactide (PLA) as a main component in which a biologically active substance is uniformly dispersed and a sustained release formulation comprising the same.

BACKGROUND ART

Recently, a microsphere or nanosphere has attracted attention as a sustained release formulation of a medicine containing a biologically active substance or the like. A microsphere generally refers to a formulation having a particle diameter of 1 μm to about 150 μm, and a formulation smaller than that having a particle diameter less than 1 μm is referred to as a nanosphere. For example, when a biologically active substance is incorporated in a biodegradable synthetic or natural polymer, the biologically active substance can be continuously released locally, or the biologically active substance can be targeted to a tissue.

A sustained release microsphere formulation which gradually releases a biologically active substance at a constant rate, needs to be, for example, a formulation in which a biodegradable polymer, a biologically active substance, an additive, a solvent and the like are appropriately controlled. In order for a sustained release microsphere formulation to effectively exhibit a pharmacological effect in vivo for a predetermined period of time, it is necessary to continuously release the biologically active substance in vivo for a predetermined period of time, by appropriately controlling the initial release amount of the biologically active substance and its release rate during a subsequent release period.

One of the important factors for determining the release rate of the biologically active substance is a kind of biodegradable polymers. Particularly, the most widely used lactic acid-glycolic acid copolymer (polylactide-co-glycolide acid, PLGA) and polylactide (PLA) being a polymer of lactic acid has a different biodegradation rate depending on its physicochemical properties such as a ratio of lactic acid and glycolic acid, its molecular weight, its affinity with water and the like, and thus, the biodegradation rate can be adjusted to a desired release period (Patent Literature 1).

Furthermore, in addition to that, a particle diameter of the microsphere and a dispersion state of the biologically active substance in the microsphere are related, in order to suppress an abnormal initial release amount (an initial burst) of a biologically active substance and to control its release rate during a release period to be constant. In spite of a problem of yield, the particle diameter of the microsphere can be adjusted to a desired particle diameter by an operation such as filtration. However, the dispersion state of the biologically active substance in the microsphere has been reported only as uniform, and has not been confirmed.

A microsphere of PLGA or PLA can be produced using, for example, a method of drying in liquid, a spray drying method, a spray freeze drying method, a drying method using a supercritical fluid process, a double emulsification method, or the like. When a biologically active substance is lipophilic, the most common production method among these methods is a method of drying in liquid in which PLGA or PLA and the biologically active substance are dissolved or dispersed in an organic solvent, mixed and emulsified with an aqueous solution in which polyvinyl alcohol (PVA) is dissolved, and the solvent is removed from the emulsion.

Patent Literature 1 discloses a method of producing a sustained release microsphere containing a biodegradable polymer such as PLGA and a peptide medicine by a spray drying method, a spray freeze drying method or a drying method using a supercritical fluid process. However, Patent Literature 1 does not describe how much the particle diameter of the sustained release microsphere varies, whether or not the peptide medicine is uniformly dispersed in the sustained release the microsphere, and whether a uniformly dispersed microsphere is obtained.

Patent Literature 2 discloses a method of producing PLGA microparticles by a method of drying in liquid using a mixed solvent comprising a halogenated hydrocarbon and a water-immiscible organic solvent having a solubility of a medicine of 0.3% (W/V) or more. Patent Literature 2 describes that particle diameters (median diameters) of the microparticles obtained in Production Examples 1 and 2 are respectively 14 and 16 but does not describe the dispersion state of the medicine in the microparticles.

Patent Literature 3 discloses PLGA nanoparticles containing a medicine. These nanoparticles are mainly intended for targeting to a specific tissue, and are nanoparticles of several tens nm to several hundreds nm which can pass through microscopic pores of blood capillaries. However, Patent Literature 3 does not describe a microsphere of 1 μm or more much larger than these nanoparticles. Even with the technique of Patent Literature 3, a person skilled in the art could not produce a microsphere having a particle diameter of 1 μm or more.

Patent Literature 4 discloses a formulation which releases leuprorelin acetate of a luteinizing hormone releasing hormone derivative, during from about 1 month to several months by subcutaneous injection. The formulation has a problem that a distribution of the particle diameters is very wide from 1 μm to 400 Therefore, Patent Literature 5 proposes as a method for solving this problem, a method of producing a microsphere in which a biologically active substance is encapsulated in a polymer for a carrier by a double emulsification method. However, Patent Literature 5 does not describe the dispersion state of the medicine in the leuprorelin acetate containing the microspheres obtained in Examples 1 to 5.

Patent Literature 6 discloses a microsphere which reduces a chronic pain for at least 28 days (672 hours). The microsphere comprises a biodegradable polymer and a local anesthetic (a biologically active substance), and releases about 75% of the local anesthetic during about 72 hours, and about 80 to 90% of the local anesthetic during about 120 hours. This suggests that the distribution of the local anesthetic in the microsphere is not uniform in the microsphere, and is biased in the outer side. From the SEM (scanning electron microscope) image of a cross section of the microsphere described in FIG. 2, the dispersion state of the local anesthetic cannot be confirmed.

Patent Literature 7 discloses a core shell structure microsphere in which a core contains solid aripiprazole, and the surface of the core is coated with a shell containing a biodegradable polymer. As described above, the microsphere of Patent Literature 7 is not a microsphere in which the biologically active substance is uniformly dispersed. Further, in the electron microscope photograph of a cross section obtained by cutting the microsphere obtained in the example shown in FIG. 5, the dispersion state of aripiprazole cannot be confirmed in the shell.

CITATION LIST

Patent Literature

Patent Literature 1: JP 2005-035994
Patent Literature 2: JP 2005-015476
Patent Literature 3: JP 4856752
Patent Literature 4: JP 2653255
Patent Literature 5: JP 2014-224114
Patent Literature 6: JP 2016-069378
Patent Literature 7: JP 2010-531303

SUMMARY OF THE INVENTION

Technical Problem

A biodegradable polymer microsphere having an average volume-based particle diameter of 1 µm or more and 150 µm or less cannot be put in practice as its release period is designed, unless the distribution of a biologically active substance (hereinafter, may be referred to as a medicine) in the microsphere is controlled. For example, when the biologically active substance is biased near the surface of the microsphere, a large amount of the biologically active substance is released from the microsphere at the initial period after administration to generate the problem of the initial burst. On the other hand, when the biologically active substance is biased in the center of the microsphere or when the microsphere is in a state of a core shell structure, the biologically active substance cannot be released continuously from the initial period. Therefore, a state in which the biologically active substance is uniformly dispersed in the microparticle, is desirable. When it is in a dispersed state in which large masses of the biologically active substance are scattered, the biologically active substance cannot be released continuously from the initial period. Similarly, when empty holes are not controlled, a similar problem occurs in the release of the biologically active substance.

When pharmacokinetics are actually investigated using a small animal such as a rat, many variations in the release rate and release profile sometimes occur. The reason is often concluded as an individual difference of rats. However, if the dispersion state of a biologically active substance in the microsphere is uniform, most of the variations will be more improved, and decomposition rate will be controlled by a kind and molecular weight of PLGA, and release of the biologically active substance from the microsphere can be realized as designed.

Uniform dispersion of the biologically active substance in the microsphere is the absolute condition for continuously releasing the biologically active substance in vivo for a predetermined period of time. However, the uniform dispersion has not been searched at present. Since the particle diameter of the microsphere is large unlike that of the nanoparticle, homogenization of the microsphere is generally difficult. Therefore, it is necessary to confirm the dispersion state of the biologically active substance in the microsphere. For that, a cross section observation sample obtained by cutting a microsphere particle is prepared, and is observed with an electron microscope at a magnification capable of confirming the biologically active substance in the microsphere or a higher magnification, so that the dispersion state can be confirmed. This can be easily performed, and is certain.

FIG. 1 is a microphotograph of the microcapsule sustained release formulation leuplin (registered trademark) for injection 1.88 mg (Takeda Pharmaceutical Company Limited), which corresponds to the sustained release microcapsule of a LH-RH derivative described in Patent Literature 4. The formulation includes various sizes of particles from large particles to small particles. FIG. 2 is an SEM (scanning electron microscope) image of a cross section of the particle of about 6 µm which was selected as a representative particle. It is understood by confirmation of an edge effect in an image, or by an EDS (energy dispersive X-ray spectrometer), that large dispersion bodies indicated by arrows in FIG. 2 are empty holes. FIG. 3 is an image prepared by dividing the SEM cross section image of FIG. 2 into six regions (Region 1 to Region 6); an averaging process in the pixel range of 3×3 using a commercial image analysis software iTEM (TEM camera control, image analysis software, EMSIS GmbH); contrast optimization by a process of highlighting the edge part; a binarization process; a process of removing noises and highlighting particles with low contrast by image processing; a second averaging process in the pixel range of 3×3; and a process of highlighting the edge part. Based on FIG. 3, a variation coefficient of the area ratios: $(s/A) \times 100$ (%), wherein A is an area of a respective divided region, and s is a sum of cross section areas of the biologically active substance included in the respective divided region, was calculated, and the variation coefficient was 1.06. By performing in this way, the dispersion state of the biologically active substance can be confirmed from the cross section. Since the variation coefficient exceeds 0.35, and the biologically active substance is not uniformly dispersed in the particle, the formulation cannot appropriately control the release rate during the release period.

Accordingly, an object of the present invention is to provide a microsphere capable of appropriately controlling the initial release amount of a biologically active substance and its release rate during a subsequent release period, and continuously releasing the biologically active substance in vivo for a predetermined period of time.

Solution to the Problem

The present inventors earnestly studied to solve the above problem. As a result of that, the present inventors have found that by a microsphere wherein a variation coefficient of the area ratios of a biologically active substance in a respective region prepared by dividing an electron microscope cross section observation image of the microsphere into six regions, is 0.35 or less, the biologically active substance is uniformly dispersed in the microsphere, empty holes are not present, and the microsphere can appropriately control the initial release amount of a biologically active substance and its release rate during a subsequent release period, and can continuously release the biologically active substance in vivo for a predetermined period of time. Thus, the present inventors have accomplished the present inventions. Namely, the present inventions are as follows.

[1] The first embodiment of the present invention is a microsphere comprising a lactic acid-glycolic acid copolymer (PLGA) or polylactide (PLA) as a main component, in which a biologically active substance is uniformly dispersed, wherein an average volume-based particle diameter of the microsphere is 1 μm to 150 μm, and a variation coefficient of area ratios in six regions is 0.35 or less, wherein the area ratios in six regions are calculated by (s/A)×100 (%) wherein the six regions are prepared by preparing a cross section observation sample obtained by cutting the microsphere; observing the cross section observation sample with an electron microscope at a magnification capable of confirming the biologically active substance in the microsphere or a higher magnification; and dividing the electron microscope observation image into six regions; and A is an area of a respective divided region, and s is a sum of cross section areas of the biologically active substance included in the respective divided region.

[2] The second embodiment of the present invention is the microsphere according to [1], wherein the biologically active substance is a lipophilic biologically active substance.

[3] The third embodiment of the present invention is the microsphere according to [1] or [2], wherein an average volume-based particle diameter of the dispersed biologically active substance is 5 nm to 500 nm.

[4] The fourth embodiment of the present invention is the microsphere according to any one of [1] to [3], wherein a content of the biologically active substance in the microsphere is 0.35 to 1.5% by mass.

[5] The fifth embodiment of the present invention is a sustained release formulation comprising the microsphere according to any one of [1] to [4].

ADVANTAGEOUS EFFECTS OF THE INVENTION

The microsphere of the present invention can appropriately control the initial release amount of a biologically active substance and its release rate during a subsequent release period, and can continuously release the biologically active substance in vivo for a predetermined period of time.

BRIEF DESCRIPTION OF THE DRAWINGS

FIG. 6-1 shows an SEM image of a cross section of the microsphere of Example 1.

FIG. 6-2 shows an image prepared by dividing the cross section image of FIG. 6-1 into six regions and a binarization process, for calculating area ratios: (s/A)×100 (%), wherein A is an area of a respective divided region, and s is a sum of cross section areas of the biologically active substance included in the respective divided region.

FIG. 7-1 shows an SEM image of a cross section of the microsphere of Example 3.

FIG. 7-2 shows an image prepared by enlarging the cross section image of FIG. 7-1 and a binarization process.

FIG. 8-1 shows an SEM image of a cross section of the microsphere of Example 4.

FIG. 8-2 shows an image prepared by dividing the cross section image of FIG. 8-1 into six regions and a binarization process, for calculating area ratios: (s/A)×100 (%), wherein A is an area of a respective divided region, and s is a sum of cross section areas of the biologically active substance included in the respective divided region.

DESCRIPTION OF THE INVENTION

1. Microsphere

Figure 1:
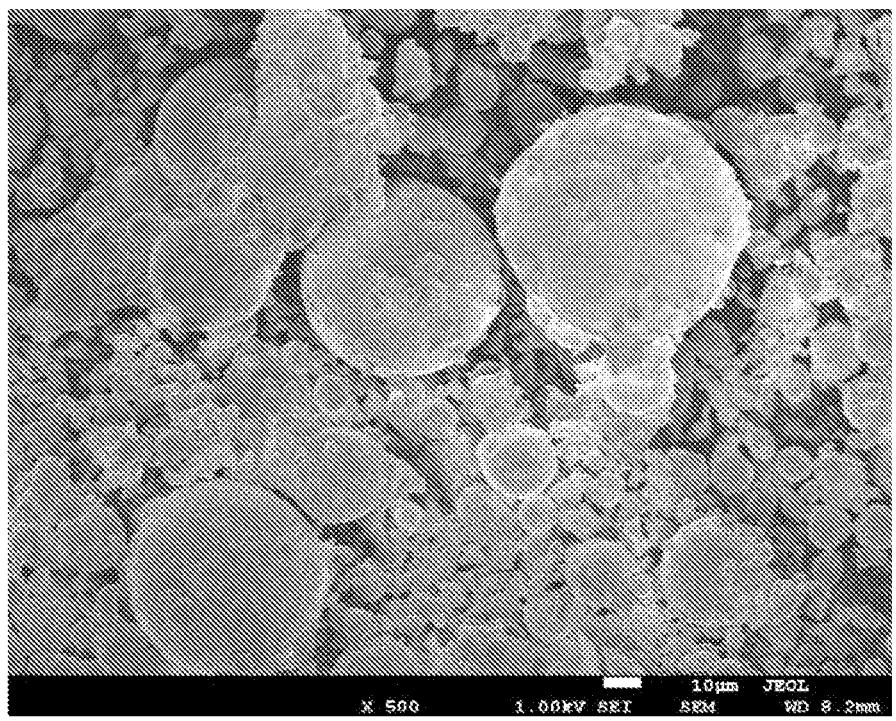
FIG. 1 shows an SEM (scanning electron microscope) image of leuplin (registered trademark) for injection 1.88 mg (Takeda Pharmaceutical Company Limited).

The microsphere of the present invention is a microsphere comprising a lactic acid-glycolic acid copolymer (PLGA) or polylactide (PLA) as a main component, in which a biologically active substance is uniformly dispersed, wherein an average volume-based particle diameter of the microsphere is 1 μm to 150 μm, and a variation coefficient of area ratios in six regions is 0.35 or less, wherein the area ratios in six regions are calculated by (s/A)×100 (%) wherein the six regions are prepared by preparing a cross section observation sample obtained by cutting the microsphere; observing the cross section observation sample with an electron microscope at a magnification capable of confirming the biologically active substance in the microsphere or a higher magnification; and dividing the electron microscope observation image into six regions; and A is an area of a respective divided region, and s is a sum of cross section areas of the biologically active substance included in the respective divided region.

When a biologically active substance is biased in the surface layer or in the center of the microsphere, or when coarse particles, aggregates or large empty holes, etc. are present in the microsphere, the above variation coefficient of area ratios becomes large. When the above variation coefficient of area ratios is 0.35 or less, a biologically active substance is uniformly dispersed. In the microsphere of the present invention, the variation coefficient of area ratios of occupation of the biologically active substance relative to the area of the respective region, in the respective region obtained by dividing a cross section of the microsphere into six regions, is 0.35 or less, preferably 0.25 or less, more preferably 0.20 or less.

The microsphere of the present invention can appropriately control the initial release amount of the biologically active substance and its release rate during a subsequent release period, and can continuously release the biologically active substance in vivo for a predetermined period of time.

<Observation of Cross Section of Microsphere>

A method of confirming a dispersion state of a biologically active substance in the microsphere is explained below.

The method can be performed by observing a cross section of the microsphere with an electron microscope at a magnification capable of clearly confirming the dispersed microparticles of the biologically active substance. The electron microscope includes a transmission electron microscope (TEM) using transmitted electrons as an information source, a scanning electron microscope (SEM) detecting secondary electrons (backscattered electrons), etc. The electron microscope may be selected according to the sample to be observed. The fine structure of nanospheres can be more observed with a transmission electron microscope. Specifically, the microsphere is coated with a thin film of gold, platinum, platinum/palladium alloy, etc. In Examples, the microspheres were coated with osmium. Then, the microsphere is first frozen with liquid nitrogen. After frozen, a cross section of FIB (focused ion beam) is prepared. That is, a cross section observation sample of the microsphere is prepared by irradiating a focused ion beam onto a sample using an FIB apparatus, and cutting out a structure at a desired position inside the sample. A preferable particle diameter of the microparticles of the biologically active substance dispersed in the base material of PLGA or PLA is several tens nm to several hundreds nm, but the particle diameter may be several μm in some cases. An entire cross section of the microsphere is observed at an observation magnification of an electron microscope capable of confirming the dispersed microparticles of the above preferable particle diameter. Usually, an observation magnification of an electron microscope is from 2,500 to several hundreds of thousands or more. In addition, in the case where a higher magnification at which the entire microsphere cannot be observed is used, the observed portions may be joined to observe the entire microsphere.

Figure 5:
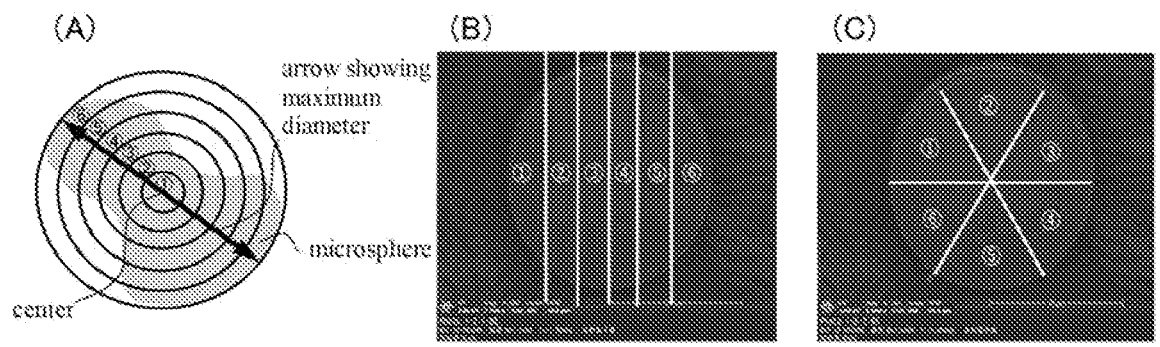
FIG. 5 shows examples of a method of dividing a microsphere. (A) shows an example of dividing it into six regions concentrically. (B) shows an example of dividing it into six regions longitudinally. (C) shows an example of dividing it into six regions latitudinally.

When the cross section image is divided into six regions, for example, as shown in FIGS. 5A to 5C, the cross section image may be divided into six regions concentrically, or may be divided into six regions in the vertical or horizontal direction, or may be divided into six regions latitudinally from the center. It is preferable to take a dividing method that remarkably shows a segregation state of the biologically active substance. For example, when dividing into six regions concentrically (FIG. 5A), it is essential to divide concentrically by dividing the radius into six equal parts from the center point of the maximum diameter of the cross section of the microsphere. When dividing into six regions in the vertical or horizontal direction (FIG. 5B), it is essential to divide into six regions at equal intervals. It is essential to divide into six regions in either direction parallel or perpendicular to the above maximum diameter. When dividing into six regions latitudinally from the center (FIG. 5C), it is essential to divide into six regions latitudinally every 60° around the center point of the above maximum diameter as a center. Depending on the constituent elements of the biologically active substance, an elementary analysis may be performed by analyzing the cross section of the microsphere using an EDS (Energy Dispersive X-ray Spectrometer), and it can be also confirmed whether or not it is an empty hole. In the case of empty holes, it should not be integrated into the area of the biologically active substance. When the EDS detection elements are not contained, the cross section observation sample may be stained with ruthenium tetroxide, osmium tetroxide, phosphotungstic acid, uranyl acetate, iodine or the like. It is also possible to identify the biologically active substance by comparison with a microsphere without the biologically active substance. The staining method is effective when it is difficult to obtain contrast in the electron microscope cross section observation image. The above are explained just as examples, and the sample may be embedded with a resin, or a microtome may be used to prepare a cross section of the microsphere.

A method of calculating a cross section area is not particularly limited, but it is preferable to use a commercial image analysis software. As a commercial image analysis software, various kind of software such as Image-Pro Plus (Media Cybernetics, Inc.), iTEM (TEM camera control, image analysis software, EMSIS GmbH), etc. can be used.

<PLGA or PLA>

PLGA is a lactic acid-glycolic acid copolymer having a constitutional unit derived from lactic acid and a constitutional unit derived from glycolic acid. PLA is a polymer of lactic acid. PLGA may comprise another biodegradable polymer such as polylactide (PLA), polyglycolide (PGA) and the like. The PLGA described herein is described as an example, and the present invention is not limited to the described PLGA.

The molar ratio (L:G) of the constitutional unit (L) derived from lactic acid and the constitutional unit (G) derived from glycolic acid in PLGA is not particularly limited, and may be appropriately selected according to the intended purpose. A preferable molar ratio (L:G) is 1:99 to 99:1, more preferably 25:75 to 99:1, further preferably 30:70 to 90:10, particularly preferably 50:50 to 85:15. Only PLA may be used. Selection of this molar ratio is important for realizing a uniform dispersion state of a biologically active substance. Selection of a molecular weight of PLGA or PLA is also similarly important.

PLGA used in the microsphere of the present invention can be produced, for example, by heating and condensation polymerization of lactic acid and glycolic acid under a weakly reduced pressure using an ion exchange resin as a catalyst. In this case, lactide may be used in place of lactic acid. PLGA may be a commercially available product. A commercially available product may be purchased from, for example, FUJIFILM Wako Pure Chemical Corporation, Taki Chemical Co., Ltd., Evonic Rohm GmbH, Merck KGaA, Sigma-Aldrich Co., LLC, and the like.

The content of PLGA or PLA in the microsphere of the present invention is not particularly limited, and may be appropriately selected according to the intended purpose. The content is preferably 1% by mass or more, more preferably 30% by mass or more and 95% by mass or less, and particularly preferably 50% by mass or more and 90% by mass or less.

<Microsphere>

The microsphere of the present invention includes PLGA or PLA and a biologically active substance. The microsphere may further contain a dispersing agent and another component, if necessary. The biologically active substance, a dispersing agent, another component and the like are dispersed in the base material of PLGA or PLA in the microsphere.

[Biologically Active Substance]

A biologically active substance contained in the microsphere of the present invention is not particularly limited, and may be appropriately selected according to the intended purpose. The biologically active substance may be, for example, a pharmaceutical compound, a functional food compound, a functional cosmetic compound, and the like. A microsphere containing a pharmaceutical compound can be suitably used, for example, as a sustained release pharmaceutical formulation. The biologically active substance includes both a lipophilic biologically active substance and a hydrophilic biologically active substance. A preferable biologically active substance includes a lipophilic biologically active substance. A lipophilic biologically active substance means, for example, a substance having a log P value of water/octanol distribution coefficient of 3 or more, and a biologically active substance not contained in a lipophilic biologically active substance is classified as a hydrophilic biologically active substance. The water/octanol distribution coefficient can be measured according to the Japanese Industrial Standard: JIS Z 7260-107 (2000): Flask shaking method. The biologically active substance is not particularly limited as long as a sustained release formulation comprising the biologically active substance is desired, and may be appropriately selected according to the intended purpose. The biologically active substance includes any form of a salt, hydrate, and the like.

The biologically active substance is uniformly dispersed in the microsphere of the present invention. By adopting such constitution, the microsphere can appropriately control the initial release amount of the biologically active substance and its release rate during a subsequent release period, and can continuously release the biologically active substance in vivo for a predetermined period of time. Uniform dispersion of the biologically active substance in the microsphere can be controlled by the content of the biologically active substance, relative to the total amount of the microsphere. A preferable content of the biologically active substance varies depending on the biologically active substance, and is, for example, 0.1 to 3% by mass, preferably 0.3 to 2% by mass, more preferably 0.35 to 1.5% by mass, further more preferably 0.5 to 1.25% by mass, relative to the total amount of the microsphere.

The average volume-based particle diameter of the dispersed microparticles of the biologically active substance is preferably 5 nm to 500 nm, more preferably 10 nm to 400 nm, and further preferably 20 nm to 200 nm.

[Dispersing Agent]

A dispersing agent may be used for dispersing the biologically active substance. The dispersing agent may be a low molecular weight dispersing agent or a high molecular weight polymer dispersing agent. A low molecular weight dispersing agent means a compound having a mass average molecular weight less than 15,000. A high molecular weight polymer dispersing agent means a compound having a mass average molecular weight of 15,000 or more, including repeated covalent bonds between one or more of monomers.

The low molecular weight dispersing agent is not particularly limited as long as it is acceptable for a pharmaceutical compound, a functional food compound, a functional cosmetic compound, and the like, and may be appropriately selected according to the intended purpose. A specific example thereof includes a lipid, a saccharide, a cyclodextrin, an amino acid, an organic acid, another component, and the like. These may be used alone or in combination of two kinds or more thereof.

The lipid is not particularly limited, and may be appropriately selected according to the intended purpose. The lipid may be, for example, a medium chain or long chain monoglyceride, diglyceride or triglyceride, a phospholipid, a vegetable oil (e.g. soybean oil, avocado oil, squalene oil, sesame oil, olive oil, corn oil, rape-seed oil, safflower oil, sunflower oil, etc.), a fish oil, a flavoring oil, a water-insoluble vitamin, a fatty acid, and a mixture thereof, a derivative thereof and the like. These may be used alone or in combination of two kinds or more thereof.

The sugar is not particularly limited, and may be appropriately selected according to the intended purpose. The sugar includes, for example, glucose, mannose, idose, galactose, fucose, ribose, xylose, lactose, sucrose, maltose, trehalose, turanose, raffinose, maltotriose, acarbose, water-soluble cellulose, synthetic cellulose, sugar alcohol, glycerin, sorbitol, lactitol, maltitol, mannitol, xylitol, erythritol, polyol, and a derivative thereof, and the like. These may be used alone or in combination of two kinds or more thereof.

The another component is not particularly limited and may be appropriately selected according to the intended purpose. The another component is preferably one which can be used for a medicine so far.

<Average Volume-Based Particle Diameter>

The average volume-based particle diameter of the microsphere of the present invention is 1 μm or more and 150 μm or less, preferably 10 μm or more and 100 μm or less, and more preferably 20 μm or more and 75 μm or less. The average volume-based particle diameter may be measured using a laser diffraction particle size distribution measuring apparatus. In the present invention, when the average volume-based particle diameter exceeds 150 the problem of an initial burst occurs due to non-uniform dispersibility of the biologically active substance in the microsphere, which tends to cause aggregation and sedimentation, and to lead to difficult processing in a subsequent step. When the average volume-based particle diameter is smaller than 1 the problem of an initial burst occurs remarkably.

The microsphere of the present invention can appropriately control the initial release amount of a biologically active substance and its release rate during a subsequent release period, and can continuously release the biologically active substance in vivo for a predetermined period of time.

2. Sustained Release Formulation

By using the microsphere of the present invention, a sustained release formulation containing the microsphere can be prepared. The sustained release formulation of the present invention can appropriately control the initial release amount of a biologically active substance and its release rate during a subsequent release period, and can continuously release the biologically active substance in vivo for a predetermined period of time, and a pharmacological effect can be effectively exhibited.

The sustained release formulation of the present invention can be simply administered as an injection, an implant or a transdermal formulation, directly to a lesion such as a muscle, subcutaneous tissue, blood vessel, organ, joint cavity, tumor, or the like. It may be administered as various other formulations. For example, when preparing a sustained-release preparation of the present invention as an injection formulation, the sustained release injection formulation as an aqueous suspension may be prepared together with a dispersing agent (Tween 80, HCO 60, carboxy methylcellulose, sodium alginate, etc.), a preservative (methylparaben, propylparaben, etc.), an isotonizing agent (sodium chloride, mannitol, sorbitol, glucose, etc.) and the like. Alternatively, the sustained release injection formulation as an oil suspension may be prepared with a vegetable oil such as soybean oil, sesame oil, corn oil, and the like.

3. Method of Producing Microsphere

<Step of Producing Microsphere>

The method of producing the microsphere of the present invention includes at least the step of forming particles, and may further include the step of filtration and sterilization, the step of removing a good solvent, and other steps, if necessary.

<Step of Forming Particles>

In the step of forming particles, it is preferable to use a pulverizing apparatus in which pulverization is performed between a plurality of processing surfaces being capable of approaching to and separating from each other, at least one of which rotates relative to the other, which is described in JP 2009-132871 or JP 2011-189348. The step of forming particles is performed, for example, by continuously feeding to the pulverizing apparatus a solution of PLGA or PLA and a biologically active substance obtained by dissolving or dispersing PLGA or PLA and the biologically active substance in a good solvent of PLGA or PLA, and a solution containing a poor solvent of PLGA or PLA to prepare emulsified particles; and removing the good solvent from the produced particles to precipitate the microsphere of the present invention. Here, "dispersing" includes dispersing the biologically active substance as a solid in a good solvent of PLGA or PLA; emulsifying the biologically active substance in a good solvent of PLGA or PLA; forming a w/o emulsion containing an aqueous solution of a hydrophilic biologically active substance and a good solvent of PLGA or PLA; and the like.

The solution of PLGA or PLA and a biologically active substance is not particularly limited as long as it is a solution in which PLGA or PLA and the biologically active substance are dissolved or dispersed in a good solvent of PLGA or PLA, and may be appropriately selected according to the intended purpose. The good solvent is not particularly limited, and may be appropriately selected according to the intended purpose. The good solvent includes, for example, a halogenated aliphatic hydrocarbon, an aliphatic ester, an alcohol, a ketone, an ether, acetonitrile, and the like. An example of the halogenated aliphatic hydrocarbon includes dichloromethane, chloroform, carbon tetrachloride, chloroethane, 2,2,2-trichloroethane, and the like. An example of the aliphatic ester includes ethyl acetate, propyl acetate, butyl acetate, and the like. An example of the alcohol includes an alcohol having low solubility in water such as benzyl alcohol, phenyl alcohol, n-butanol, and the like. An example of the ketone includes a ketone having 3 to 6 carbon atoms (e.g., acetone, methyl ethyl ketone, methyl isobutyl ketone, cyclohexanone, etc.), and the like. An example of the ether includes an ether having 2 to 6 carbon atoms (e.g., dimethyl ether, methyl ethyl ether, diethyl ether, etc.), and the like. It is preferable to select a solvent having low solubility in water, from the view point of the content of the biologically active substance and for the purpose of preventing an initial burst. A good solvent is preferably a halogenated aliphatic hydrocarbon, a ketone, and a mixture thereof, more preferably dichloromethane, acetone and a mixture thereof. These may be used alone or in combination of two kinds or more thereof. The particle diameter can be controlled by changing a kind of the solvent or a mixing amount of the solvent.

A good solvent means a solvent having high solubility of PLGA or PLA, and a poor solvent means a solvent having low or no solubility of PLGA or PLA. A good solvent and a poor solvent are selected so that the biologically active substance is not biased in each microsphere, and a coarse particle or an aggregate of particles is not generated. In addition, a good solvent and a poor solvent can be defined by, for example, a quantity of PLGA or PLA which can be dissolved in 100 g of the solvent at 25° C. In the present invention, the good solvent is preferably a solvent which dissolves 0.1 g or more, more preferably 0.2 g or more, and still more preferably 0.5 g or more of PLGA or PLA. The poor solvent is preferably a solvent which dissolves only 0.05 g or less, more preferably 0.02 g or less, and still more preferably 0.01 g or less of PLGA or PLA. The poor solvent is not particularly limited, and may be appropriately selected according to the intended purpose, and water is preferable.

A content of PLGA or PLA in a solution of PLGA or PLA and a biologically active substance may be changed depending on the good solvent, depending on the particle diameter of the intended microsphere, so that the biologically active substance is uniformly dispersed in the microsphere. The content of PLGA or PLA is, for example, 1 to 30% by mass, preferably 3 to 20% by mass, and more preferably 5 to 15% by mass. The content of the biologically active substance in the solution of PLGA or PLA may be appropriately changed according to the intended purpose, the pharmacological effect and the like, so that the biologically active substance is uniformly dispersed in the microsphere.

A stabilizer may be added to the poor solvent for further ensuring stability of the produced microsphere. The stabilizer is not particularly limited, and may be appropriately selected according to the intended purpose. The stabilizer includes, for example, polyvinyl alcohol (PVA), polyvinyl pyrrolidone (PVP), carboxy methylcellulose (CMC), hydroxypropylcellulose (HPC), hydroxypropylmethylcellulose (HPMC), lecithin, Polysorbate 80, and the like, and polyvinyl alcohol (PVA) is preferable. Further, the concentration of the added stabilizer is preferably 0.01 to 20% by mass, more preferably 5% by mass or less. The preferable poor solvent is, for example, an aqueous solution of PVA, and the like.

The solution of PLGA of PLA and a biologically active substance and the solution of a poor solvent is desirably prepared using a preparation apparatus such as a rotatory dispersing apparatus which realizes uniform mixing by applying a shearing force to a fluid, for example, by rotating a stirring bar of various shapes such as a rod, a plate and a propeller in a tank, or by equipping with a screen rotating relative to a stirring bar. A stirring apparatus disclosed in JP 5147091 may be applied as a preferable example of the rotatory dispersing apparatus. It is necessary to thoroughly mix the solution of PLGA or PLA and the poor solvent, for uniformly dispersing the biologically active substance in the microsphere. For complete mixing, it is necessary to aim at homogenization at least on a molecular level. Incomplete mixing causes un-uniform dispersion state.

The rotatory dispersing apparatus may be a batch type one or a continuous type one. When performed by a continuous type rotatory dispersing apparatus, a stirring energy can be appropriately controlled, by using an apparatus to continuously supply and discharge a fluid to and from the stirring tank, or using a continuous mixer without using a stirring tank, or using a known stirring apparatus or a stirring means.

Incidentally, the stirring energy is described in detail in JP H04-114725 by the present applicant. The stirring method in the present invention is not particularly limited, but may be performed using a various shearing type, friction type, high-pressure jet type, ultrasonic type, etc, of a stirrer, a dissolver, an emulsifier, a disperser, a homogenizer, or the like. An example thereof includes a continuous type emulsifier such as ULTRA-TURRAX (IKA-Werke GmbH & Co. KG), POLYTRON (Kinematica AG), TK HOMOMIXER (Primix Corporation), Ebara Milder (Ebara Corporation), TK HOMOMETIC LINE FLOW (Primix Corporation), Colloid Mill (Kobelko Eco-Solutions, Co., Ltd.), Slasher (NIPPON COKE & ENGINEERING, Co., Ltd.), Trigonal Wet Pulverizer (Mitsui Miike Chemical Engineering Machinery, Co., Ltd.), Cavitron (Euro Tech, Co., Ltd.), Fine Flow Mill (Pacific Machinery & Engineering, Co., Ltd.), and the like; a batch type or continuous dual type emulsifier such as Clearmix (M. Technique Co., Ltd.), Clearmix Dissolver (M. Technique Co., Ltd.), and the like. Further, it is desirable to use a stirring apparatus equipped with a stirring blade rotating at high speed and equipped with a screen outside of the stirring blade which discharges a fluid as a jet stream from an opening of the screen, particularly, the above Clearmix (M. Technique Co., Ltd.) and Clearmix Dissolver (M. Technique Co., Ltd.).

In the above pulverizing apparatus, it is possible to control the particle diameter and the particle diameter distribution of microparticles of PLGA or PLA by adjusting the contact pressure of the rotating processing surfaces at a standstill period. As a result of experiments by the present inventors, the contact pressure is preferably 20 $g/cm^2$ to 250 $g/cm^2$. When the contact pressure is lower than 20 $g/cm^2$, the thin film is not stable and the particle diameter distribution becomes wide. When the contact pressure is higher than 250 $g/cm^2$, it has been found difficult to adjust the intended particle diameter. The contact pressure may be preferably 50 $g/cm^2$ to 200 $g/cm^2$, and more preferably 80 $g/cm^2$ to 150 $g/cm^2$.

It is preferable to prevent coalescence of the respective microspheres formed by contacting the solution of PLGA or PLA and the biologically active substance with the solution containing the poor solvent. As a method of preventing the coalescence, the solution containing a poor solvent is preferably added in a tank for recovering a solution discharged fluid beforehand, and is slowly stirred. By stirring, the coalescence of the microspheres can be further suppressed. A rotatory dispersing apparatus is preferable for stirring, and Clearmix Dissolver (M. Technique Co., Ltd.) is desirable. The rotatory dispersing apparatus is not particularly limited as long as the whole solution can be made to flow mildly. When stirring is strong, the emulsified particles of PLGA or PLA may break down, the distribution width may become wider, and the dispersion state of the biologically active substance may collapse.

When a biologically active substance is a lipophilic biologically active substance, the step of forming particles can be suitably performed according to the above description, and a microsphere can be manufactured. When a biologically active substance is a hydrophilic biologically active substance, the hydrophilic biologically active substance is dispersed in a good solvent of PLGA or PLA using, for example, a dispersing agent, whereby the step of forming particles can be similarly performed to produce a microsphere.

In addition, when a biologically active substance is a hydrophilic biologically active substance, the hydrophilic biologically active substance is dissolved in an aqueous solvent such as water together with a stabilizer, if necessary, and is mixed with a solution in which PLGA or PLA is dissolved in a good solvent of PLGA or PLA, to prepare a w/o emulsion; and the above step of forming particles is performed using the w/o emulsion as a solution of PLGA or PLA and the biologically active substance, and using the above pulverizing apparatus. For preparing the w/o emulsion, an intermittent shaking method, a propeller type stirring apparatus, a method by a mixer using a turbine type stirring apparatus, a colloid mill method, a homogenizer method, and an ultrasonic irradiation method can be used. Using the above pulverizing apparatus, this w/o emulsion of the solution of PLGA or PLA and a physiologically active substance, and a solution containing a poor solvent of PLGA or PLA are continuously added to prepare emulsified particles as a w/o/w emulsion; and the good solvent is removed from the produced particles to precipitate the microsphere of the present invention. This obtained microsphere may be used as it is, but it is also possible to further add an excipient (mannitol, sorbitol, lactose, glucose, etc.), redisperse the mixture, and freeze dry or spray dry the mixture, to be solidified. A more stable sustained release injection formulation can be obtained, by adding distilled water for injection or an appropriate dispersion medium to this solidified microsphere when used.

<Step of Filtration and Sterilization>

Sterile filtration of the prepared solution containing PLGA or PLA and a biologically active substance agent and the solution of a poor solvent is preferably performed prior to the step pf forming particles, if desired. The solution containing a poor solvent can be sterilized by filtration using a hydrophilic filter, and the solution of PLGA or PLA and a biologically active substance can be sterilized by filtration using a hydrophobic filter. A bore diameter of the filters used for filtration is preferably 0.1 μm to 0.45 μm, more preferably 0.2 μm.

The above filter for sterile filtration is not particularly limited, and may be appropriately selected according to the intended purpose. For example, for sterile filtration of the solution containing a poor solvent, a hydrophilic filter such as polyvinylidene fluoride (PVDF) and polyethersulfone may be used. For sterile filtration of the solution of PLGA or PLA and a biologically active substance, a hydrophobic filter such as polytetrafluoroethylene (PTFE) may be used. The filter for sterile filtration is not limited to the material described here, but it is necessary to be selected depending on adsorption of the medicine and a kind of the solvent.

<Step of Removing a Good Solvent>

In the step of removing a good solvent, a good solvent is removed from the emulsified particles containing PLGA or PLA and a biologically active substance. The step of removing a good solvent is not particularly limited, and may be appropriately selected according to the intended purpose, as long as the good solvent can be removed from the emulsified particles in the state that a biologically active substance is uniformly dispersed in the microsphere. The step of removing a good solvent includes, for example, a method of evaporating and removing the good solvent from the fluid, by at least one of heating the fluid with stirring, flowing a gas such as nitrogen on a surface of the fluid, and reducing a pressure of the fluid. Flowing a gas such as nitrogen on a surface of the fluid is preferable. It is preferable in many cases to remove a good solvent quickly for maintaining the state that a biologically active substance is uniformly dispersed in the microsphere. It is preferable in some cases to remove a good solvent slowly. A time of removing the good solvent may be, for example, 30 minutes to 12 hours, preferably 1 to 10 hours, and more preferably 1 to 5 hours.

A temperature in removing a good solvent depends on a kind of the good solvent. It is necessary to perform at a suitable temperature between a high temperature near the boiling point of the good solvent and a low temperature, while observing a cross section of the microsphere. When a concentration of PLGA or PLA is low, it is often seen that a volume of particles significantly changes during removing a good solvent, and the biologically active substance dispersed in advance aggregates then. Attention should be paid to that.

<Other Steps>

Other steps include, for example, a solvent composition preparation, a classification step, a particle cleaning step, and the like. Normally, coarse powder cut or fine powder cut is performed in the classification step, but the particles produced in the present invention do not substantially need the classification step. However, a classification step may be included just in case.

By the above production method, it is possible to produce a microsphere having a particle diameter of 1 μm to 150 μm in which a biologically active substance is uniformly dispersed. Namely, it is possible to produce a microsphere wherein a variation coefficient of area ratios in six regions is 0.35 or less, wherein the area ratios in six regions are calculated by $(s/A) \times 100$ (%) wherein the six regions are prepared by preparing a cross section observation sample obtained by cutting the microsphere; observing the cross section observation sample with an electron microscope at a magnification capable of confirming the biologically active substance in the microsphere or a higher magnification; and dividing the observed image into six regions; and A is an area of a respective divided region, and s is a sum of cross section areas of the biologically active substance included in the respective divided region.

EXAMPLE

Hereinafter, the present invention is explained in more detail with reference to Examples, but the present invention is not limited only to these Examples.

Reference Example 1

In Reference Example 1, microspheres (PLGA microparticles) without a biologically active substance were prepared. Using the microspheres of Reference Example 1 as an index, cross sections of the microspheres of Examples and Comparative Examples were observed as SEM images, and the dispersion states of the biologically active substance in the microspheres of Examples and Comparative Examples were confirmed below.

<Preparation of PLGA Solution and Aqueous PVA Solution>

Dichloromethane (Kanto Chemical Co., Inc.) was added to lactic acid-glycolic acid copolymer (Resomer RG504, Evonik AG) so that the concentration was 13% by mass. Lactic acid-glycolic acid copolymer was dissolved using a high-speed rotatory dispersing apparatus Clearmix Dissolver (M. Technique Co., Ltd.) to obtain PLGA solution. Thereafter, the solution was filtrated with a 0.2 μm vent filter (φ 62, Merck KGaA). Ion exchanged water was added to polyvinyl alcohol (PVA, EG-40P, Nippon Synthetic Chemical Industry Co., Ltd.) so that the concentration was 1.5% by mass, and polyvinyl alcohol was dissolved using a high-speed rotatory dispersing apparatus Clearmix (M. Technique Co., Ltd.) to obtain an aqueous PVA solution. Thereafter, the solution was filtrated with a hydrophilic PVDF membrane filter (φ 47, Merck KGaA). The aqueous PVA solution was added in a tank for collecting PLGA emulsified particles beforehand, and was slowly stirred to an extent that the solution surface just moved.

<Preparation of Microsphere (PLGA Microparticles)>

As the step of forming particles, the prepared PLGA solution and the aqueous PVA solution were mixed using the pulverizing apparatus described in JP 2011-189348. Here, the pulverizing apparatus described in JP 2011-189348 is an apparatus described in FIG. 25 of the publication, in which the opening of the second part d20 has a concentric annular shape which is surrounding the central opening of the processing surface 2 which is a ring-shaped disc, and a disk diameter is 75 mm. Specifically, the prepared aqueous PVA solution was introduced from the first introduction path d1 into the space between the processing surfaces 1 and 2 at 0.02 MPaG, at 65 mL/min and at 30° C., and the prepared PLGA solution was introduced from the second introduction path d2 into the space between the processing surfaces 1 and 2 at 0.65 MPaG, at 20 mL/min and at 30° C. at the rotational speed of the processing member 10 of 2,000 rpm, and the aqueous PVA solution and the PLGA solution were mixed in a forced thin film to prepare PLGA emulsified particles containing dichloromethane into the space between the processing surfaces 1 and 2. The fluid containing PLGA emulsified particles (hereinafter, PLGA emulsified particle dispersion) in the space between the processing surfaces 1 and 2 was discharged from the space between the processing surfaces 1 and 2 of the pulverizing apparatus. The discharged PLGA emulsified particle dispersion was collected in a recovery tank.

Next, as the step of removing a solvent, argon gas was blown onto the fluid surface to remove dichloromethane over 3.5 hours, while stirring the discharged fluid at a peripheral speed of 4.7 m/sec using Clearmix Dissolver (M. Technique Co., Ltd.), to obtain a suspension containing PLGA microparticles (PLGA microparticle suspension). The average volume-based particle diameter of the obtained PLGA microparticles was 34.0 Representative particles were frozen with liquid nitrogen, and an FIB cross section was prepared, and an SEM image (FIG. 4) was observed.

Figure 4:
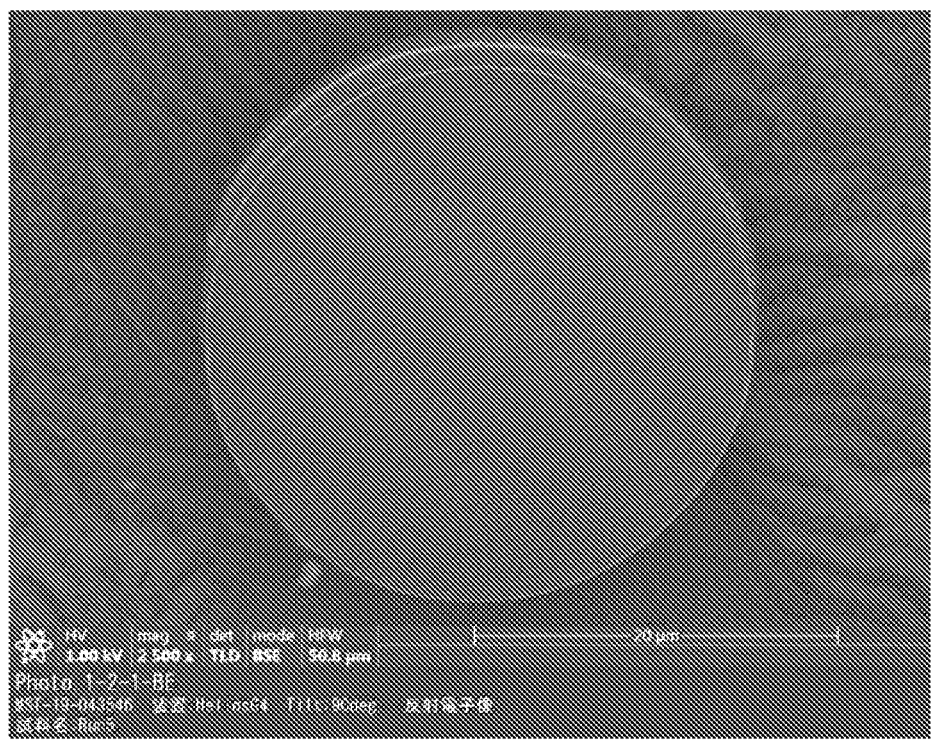
FIG. 4 shows an SEM image of a cross section of the microsphere without a biologically active substance of Reference Example 1.

As shown in FIG. 4, it was confirmed that a particle-like mass or an empty hole was not present in the FIB section. Further, it was found that the cross section of the microsphere of Reference Example 1 could be used as an index in observation of cross sections of the microspheres of Examples and Comparative examples.

Example 1

<Preparation of Solution of PLGA and Biologically Active Substance and Aqueous PVA Solution>

64.5% by mass of dichloromethane (Kanto Chemical Co., Inc.) and 25% by mass of acetone (Kanto Chemical Co., Inc.) were added to lactic acid-glycolic acid copolymer (Resomer RG752H, Evonik AG) and curcumin (FUJIFILM Wako Pure Chemical Corporation, Wako special grade) as a biologically active substance, so that the concentration of lactic acid-glycolic acid copolymer was 10% by mass, and the concentration of curcumin was 0.5% by mass. Lactic acid-glycolic acid copolymer and curcumin were dissolved using a high-speed rotatory dispersing apparatus Clearmix Dissolver (M. Technique Co., Ltd.) to obtain a solution of PLGA and the biologically active substance. Thereafter, the solution was filtrated with a 0.2 μm air vent filter (φ 62, Merck KGaA). An aqueous PVA solution was prepared in the same manner as in Reference Example 1. The aqueous PVA solution was added in a tank for collecting emulsified particles of PLGA and the biologically active substance beforehand, and was slowly stirred to an extent that the solution surface just moved.

<Preparation of Microsphere>

As the step of forming particles, the prepared solution of PLGA and the biologically active substance and the aqueous PVA solution were mixed using the pulverizing apparatus described in JP 2011-189348 in the same manner as in Reference Example 1. Specifically, the prepared aqueous PVA solution was introduced from the first introduction path d1 into the space between the processing surfaces 1 and 2 at 0.0 MPaG, at 50 mL/min and at 25° C., and the prepared solution of PLGA and the biologically active substance was introduced from the second introduction path d2 into the space between the processing surfaces 1 and 2 at 0.3 MPaG, at 16 mL/min of 25° C. at the rotational speed of the processing member 10 of 5,000 rpm, and the aqueous PVA solution and the solution of PLGA and the biologically active substance were mixed in a forced thin film to prepare emulsified particles of PLGA and the biologically active substance containing dichloromethane in the space between the processing surfaces 1 and 2. The fluid containing the emulsified particles of PLGA and the biologically active substance (hereinafter, emulsified particle dispersion of PLGA and the biologically active substance) in the space between the processing surfaces 1 and 2 was discharged from the space between the processing surfaces 1 and 2 of the pulverizing apparatus. The emulsified particle dispersion of PLGA and the biologically active substance was collected in a recovery tank keeping the pressure of 0.03 MPaG for collecting the discharged emulsified particle dispersion of PLGA and the biologically active substance.

Figure 2:
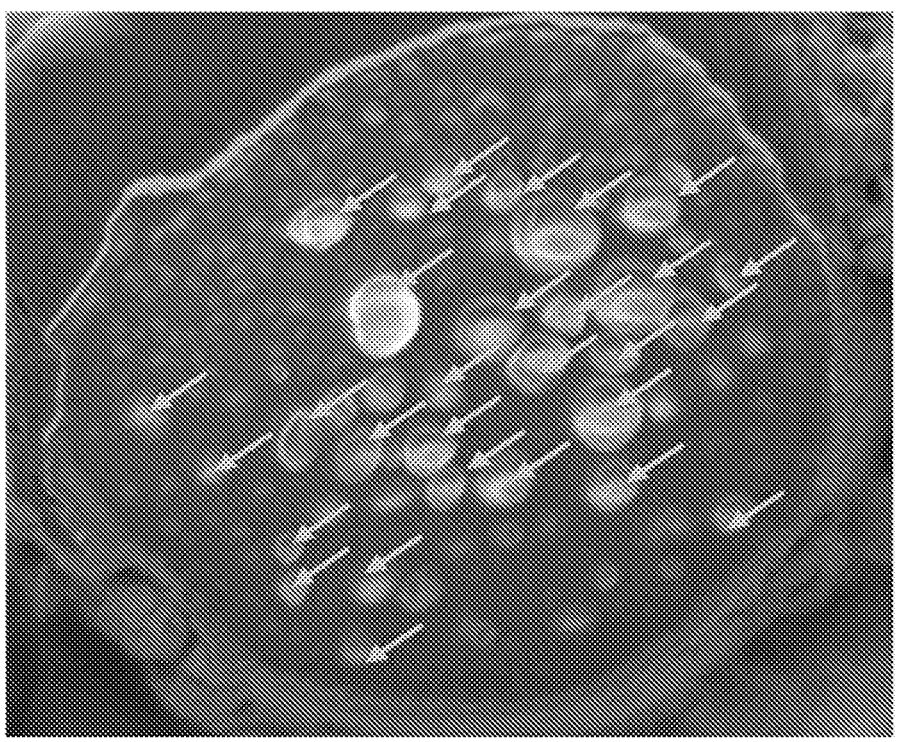
FIG. 2 shows an SEM image of a cross section of a representative particle of leuplin (registered trademark) for injection 1.88 mg (Takeda Pharmaceutical Company Limited).
Figure 3:
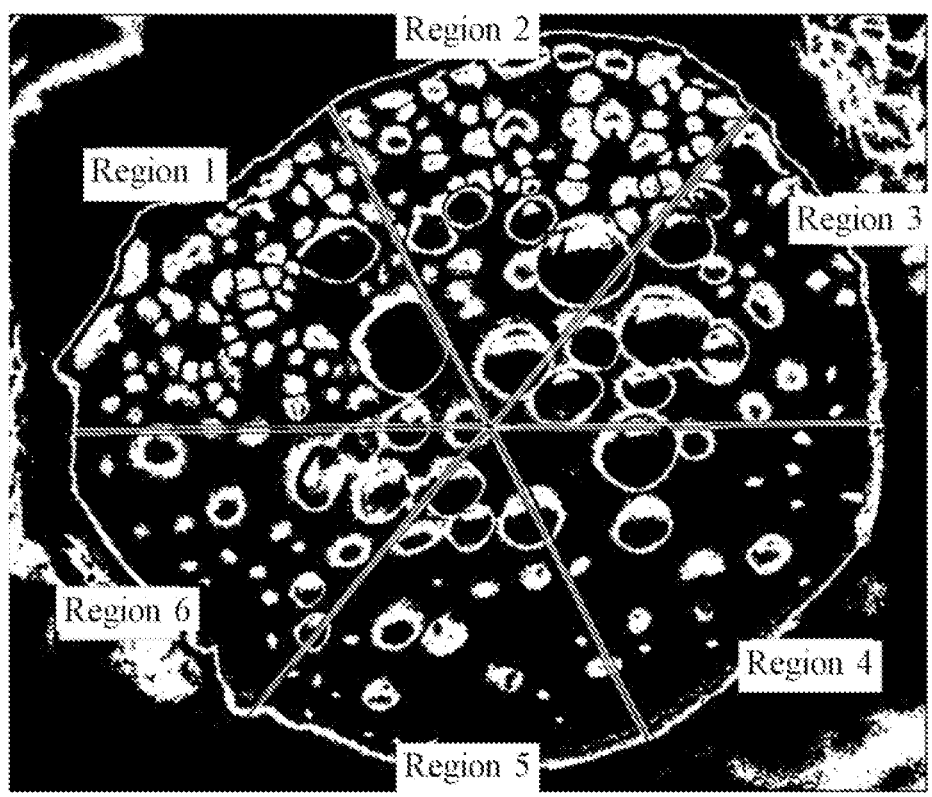
FIG. 3 shows an image prepared by dividing the cross section image of FIG. 2 into six regions and a binarization process, for calculating area ratios: (s/A)×100 (%), wherein A is an area of a respective divided region, and s is a sum of cross section areas of the biologically active substance included in the respective divided region.
Figures 1, 6:
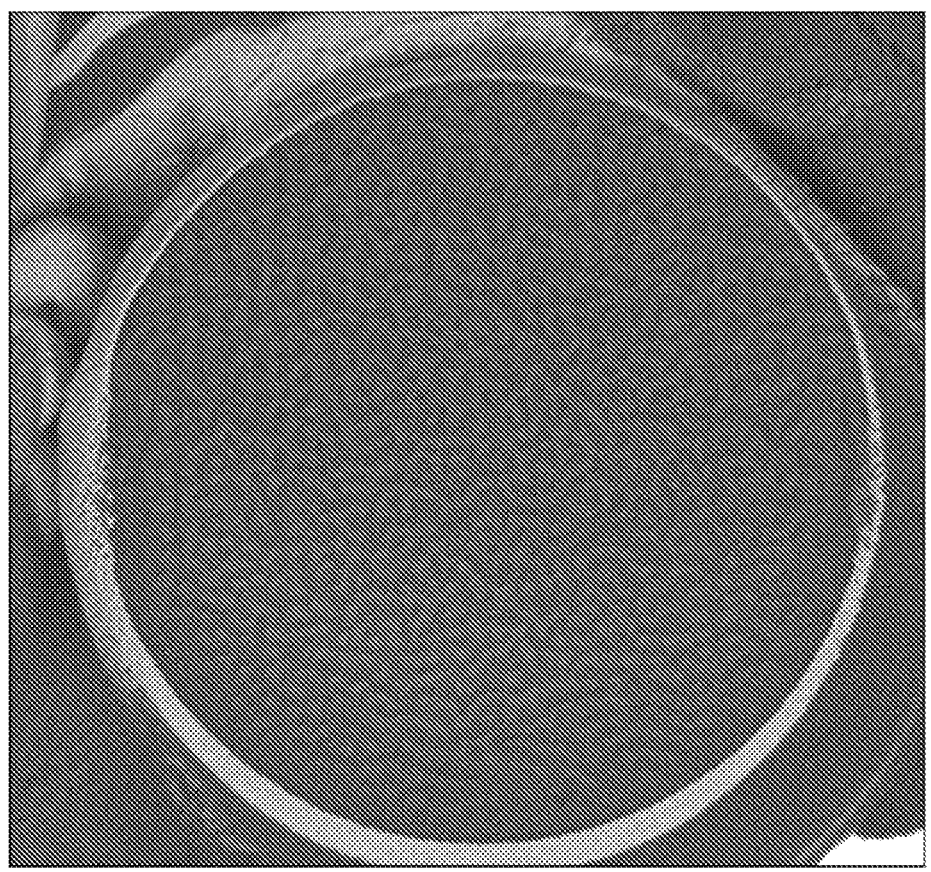
Figures 2, 6:
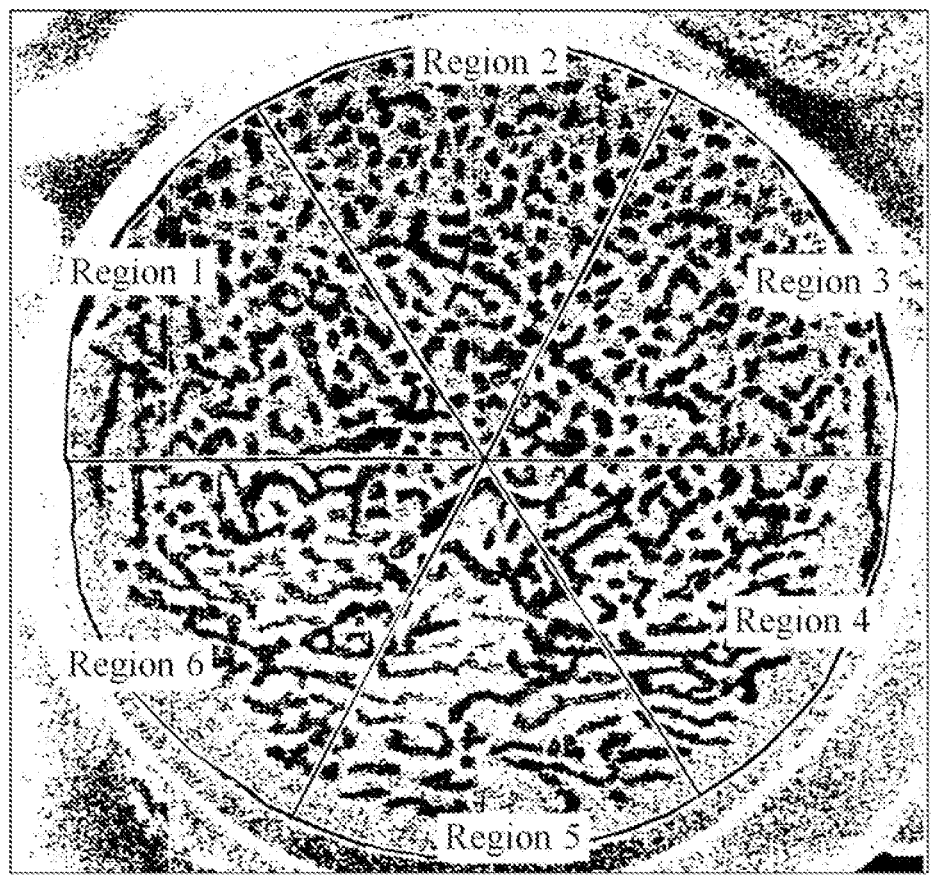

Next, as the step of removing a solvent, argon gas was blown on the fluid surface to remove dichloromethane and acetone over 3.5 hours, while stirring the discharged fluid at a peripheral speed of 4.7 m/sec using Clearmix Dissolver (M. Technique Co., Ltd.), to obtain a suspension containing microspheres (microsphere suspension). The average volume-based particle diameter of the obtained microspheres was 7.5 Representative particles were frozen with liquid nitrogen, and an FIB cross section was prepared, and an SEM image (FIG. 6-1) was observed. To the obtained particle cross section of the SEM image, was averaging process performed in the pixel range of 3×3 using a commercial image analysis software iTEM (TEM camera control, image analysis software, EMSIS GmbH); and contrast optimization was performed by a process of highlighting the edge part. Then, a binarization process, and a process of removing noises and highlighting particles with low contrast by image processing were performed; and a second averaging process in the pixel range of 3×3, and a process of highlighting the edge part were performed. FIG. 6-2 shows an image in which the particle cross section was divided into six regions (Region 1 to Region 6) on the image latitudinally every 60° around the center point of the maximum diameter as a center.

The variation coefficient of the area ratios: $(s/A) \times 100$ (%), wherein A is an area of a respective divided region, and s is a sum of cross section areas of the biologically active substance included in the respective divided region, in the FIB cross section of curcumin particles of FIG. 6-2, was 0.161.

Example 2

A suspension containing microspheres was prepared in the same manner as in Example 1 except that polylactic acid (Resomer R202H, Evonik AG) was used instead of lactic acid-glycolic acid copolymer (Resomer RG752H, Evonik AG). The average volume-based particle diameter of the obtained microspheres was 7.3 Representative particles were frozen with liquid nitrogen, and an FIB cross section was prepared, and an SEM image was observed.

The observed SEM image was image analyzed in the same manner as in Example 1. The variation coefficient of the area ratios: $(s/A) \times 100$ (%), wherein A is an area of a respective divided region, and s is a sum of cross section areas of the biologically active substance included in the respective divided region, was 0.214.

Example 3

Dichloromethane (Kanto Chemical Co., Inc.) was added to lactic acid-glycolic acid copolymer (Resomer RG504, Evonik AG) and progesterone (Sigma-Aldrich Co., LLC) as a biologically active substance, so that the concentration of lactic acid-glycolic acid copolymer was 13% by mass, and the concentration of progesterone was 1.0% by mass. Lactic acid-glycolic acid copolymer and progesterone were dissolved using a high-speed rotatory dispersing apparatus Clearmix Dissolver (M. Technique Co., Ltd.) to obtain a solution of PLGA and the biologically active substance. Thereafter, the solution was filtrated with a 0.2 μm air vent filter (φ 62, Merck KGaA). An aqueous PVA solution was prepared in the same manner as in Reference Example 1. The aqueous PVA solution was added in a tank for collecting emulsified particles of PLGA and the biologically active substance beforehand, and was slowly stirred to an extent that the solution surface just moved.

<Preparation of Microsphere>

As the step of forming particles, the prepared solution of PLGA and the biologically active substance and the aqueous PVA solution were mixed using the pulverizing apparatus described in JP 2011-189348 in the same manner as in Reference Example 1. Specifically, the prepared aqueous PVA solution was introduced from the first introduction path d1 into the space between the processing surfaces 1 and 2 at 0.0 MPaG, at 50 mL/min and at 30° C., and the prepared solution of PLGA and the biologically active substance was introduced from the second introduction path d2 into the space between the processing surfaces 1 and 2 at 0.35 MPaG, at 16 mL/min of 30° C. at the rotational speed of the processing member 10 of 1,700 rpm, and the aqueous PVA solution and the solution of PLGA and the biologically active substance were mixed in a forced thin film to prepare emulsified particles of PLGA and the biologically active substance containing dichloromethane in the space between the processing surfaces 1 and 2. The fluid containing the emulsified particles of PLGA and the biologically active substance (hereinafter, emulsified particle dispersion of PLGA and the biologically active substance) in the space between the processing surfaces 1 and 2 was discharged from the space between the processing surfaces 1 and 2 of the pulverizing apparatus. The emulsified particle dispersion of PLGA and the biologically active substance was collected in a recovery tank keeping the pressure of 0.02 MPaG for collecting the discharged emulsified particle dispersion of PLGA and the biologically active substance.

The step of removing a solvent was performed in the same manner as in Examples 1 and 2. The average volume-based particle diameter of the obtained microspheres was 34.8 Representative particles were frozen with liquid nitrogen, and an FIB cross section was prepared, and an SEM image (FIG. 7-1) was observed.

Figures 1, 7:
Figures 2, 7:

The observed SEM image was image analyzed in the same manner as in Examples 1 and 2. FIG. 7-2 shows an image prepared by enlarging the SEM image and a binarization process The variation coefficient of the area ratios: (s/A)×100 (%), wherein A is an area of a respective region obtained by dividing into six regions on the SEM image latitudinally every 60° around the center point of the maximum diameter as a center, and s is a sum of cross section areas of the biologically active substance included in the respective divided region, was 0.056.

Example 4

Dichloromethane (Kanto Chemical Co., Inc.) was added to lactic acid-glycolic acid copolymer (Resomer RG504, Evonik AG) and probcol (FUJIFILM Wako Pure Chemical Corporation, for cell biochemistry) as a biologically active substance, so that the concentration of lactic acid-glycolic acid copolymer was 13% by mass, and the concentration of probcol was 1.0% by mass. Lactic acid-glycolic acid copolymer and probcol were dissolved using a high-speed rotatory dispersing apparatus Clearmix Dissolver (M. Technique Co., Ltd.) to obtain a solution of PLGA and the biologically active substance. Thereafter, the solution was filtrated with a 0.2 μm air vent filter (φ 62, Merck KGaA). An aqueous PVA solution was prepared in the same manner as in Reference Example 1. The aqueous PVA solution was added in a tank for collecting emulsified particles of PLGA and the biologically active substance beforehand, and was slowly stirred to an extent that the solution surface just moved.

The step of removing a solvent was performed in the same manner as in Examples 1 to 3. The average volume-based particle diameter of the obtained microspheres was 32.5 μm. Representative particles were frozen with liquid nitrogen, and an FIB cross section was prepared, and an SEM image (FIG. 8-1) was observed.

Figures 1, 8:
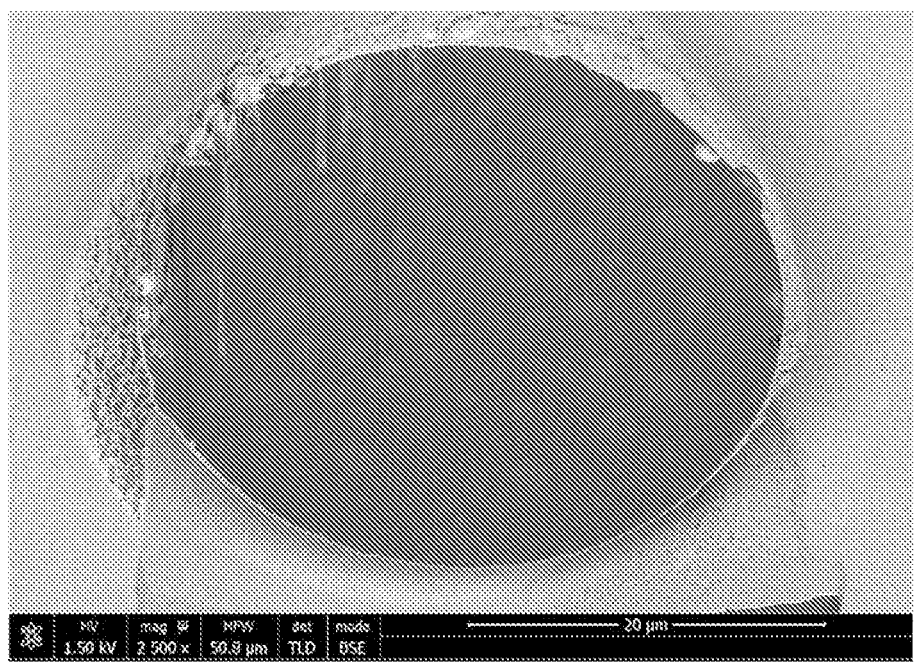
Figures 2, 8:
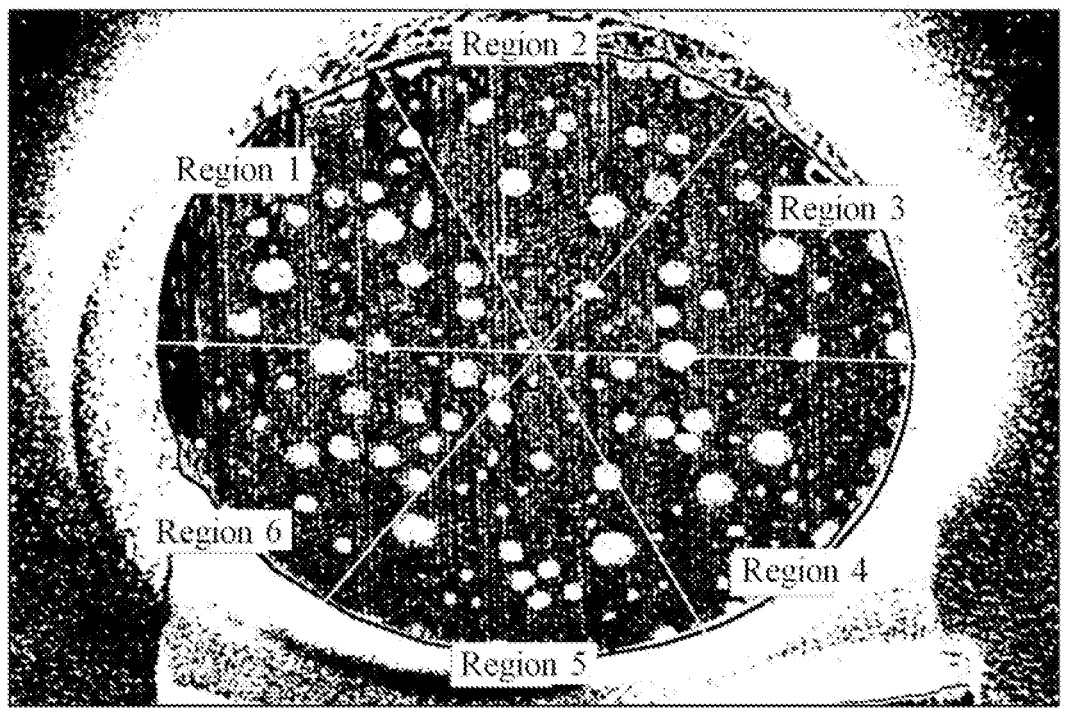

The observed SEM image was image analyzed in the same manner as in Example 4. FIG. 8-2 shows an image prepared by a binarization process The variation coefficient of the area ratios: (s/A)×100 (%), wherein A is an area of a respective region obtained by dividing into six regions on the SEM image latitudinally every 60° around the center point of the maximum diameter as a center, and s is a sum of cross section areas of the biologically active substance included in the respective divided region, was 0.235.

Comparative Example 1

As the step of forming particles, an emulsified particle dispersion of PLGA and the biologically active substance was prepared in the same manner as in Examples 1 and 2. Next, as the step of removing a solvent, dichloromethane was removed in the atmosphere from the collected discharged fluid over 42 hours, while stirring the discharged fluid at a peripheral speed of 4.7 m/sec using Clearmix Dissolver (M. Technique Co., Ltd.), to obtain a suspension containing microspheres (microsphere suspension). The average volume-based particle diameter of the obtained microspheres was 31.8 μm. Representative particles were frozen with liquid nitrogen, and an FIB cross section was prepared, and an SEM image was observed.

Figure 9:
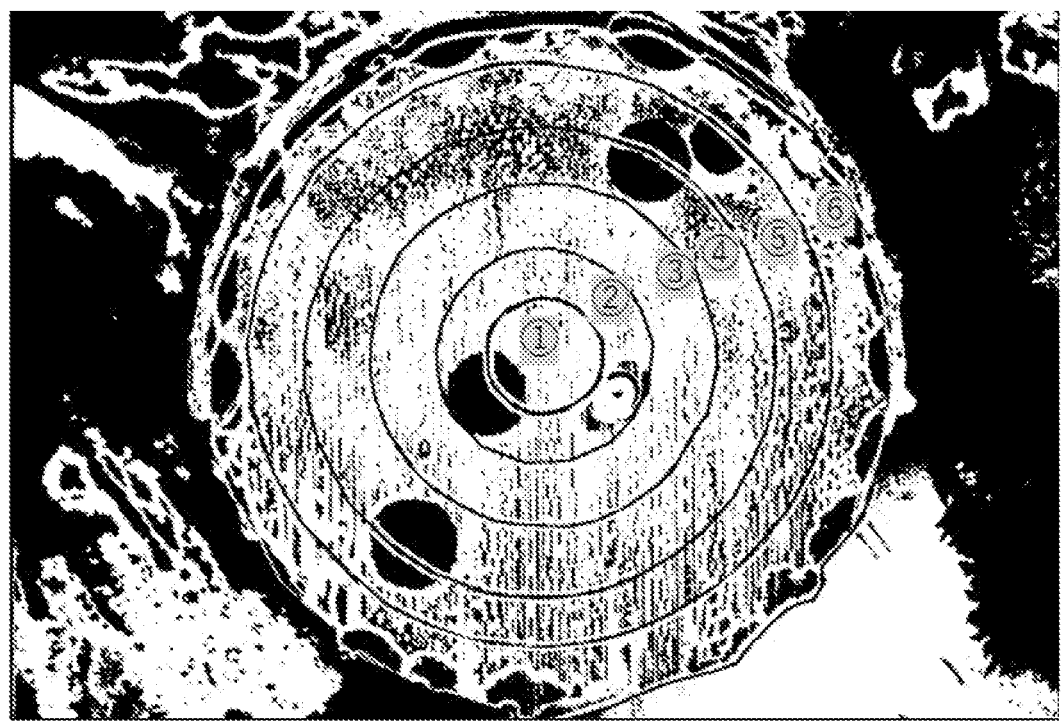
FIG. 9 shows an image prepared by dividing the cross section image of Reference Example 1 into six regions and a binarization process, for calculating area ratios: (s/A)×100 (%), wherein A is an area of a respective divided region, and s is a sum of cross section areas of the biologically active substance included in the respective divided region.

The observed SEM image was image analyzed in the same manner as in Examples 1 to 3. FIG. 9 shows an image prepared by a binarization process The variation coefficient of the area ratios: (s/A)×100 (%), wherein A is an area of a respective region obtained by dividing into six regions on the SEM image concentrically by dividing the radius into six equal parts from the center point of the maximum diameter, and s is a sum of cross section areas of the biologically active substance included in the respective divided region, was 0.468.

Comparative Example 2

Figure 10:
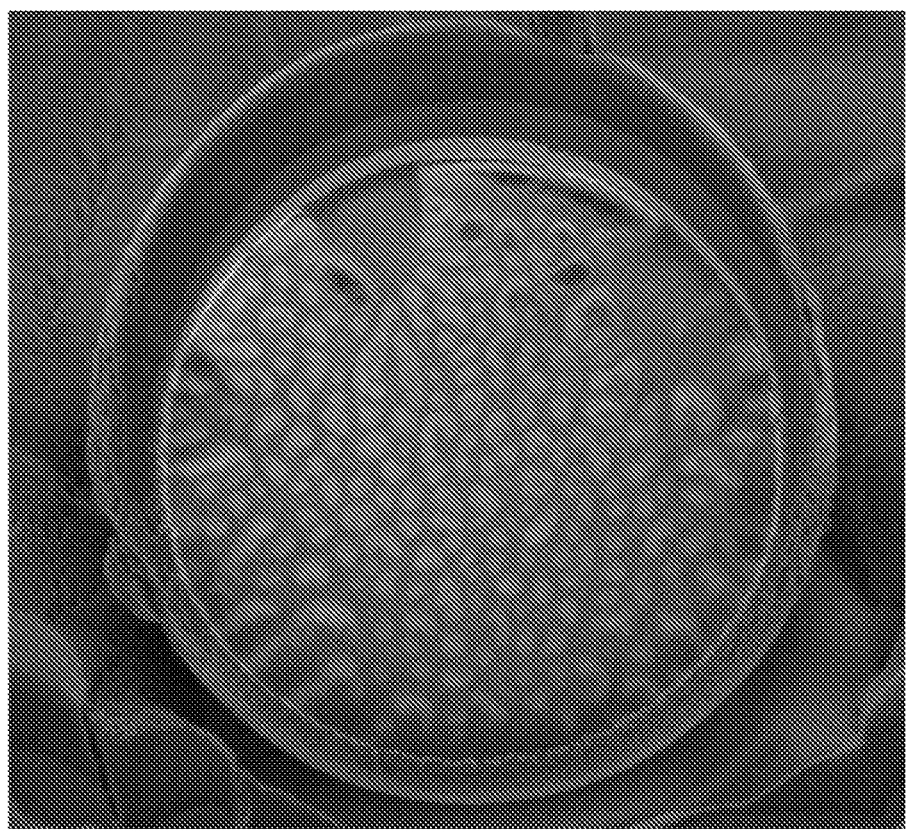
FIG. 10 shows an SEM image of a cross section of the microsphere of Comparative Example 2.

A dispersion containing microspheres was prepared with the same formulation as in Example 4, by performing the step of forming particles and the step of removing a solvent under the same conditions as in Example 4, except that dissolution of PLGA and the medicine was performed by stirring for 10 minutes with a propeller type stirring apparatus (Three-One Motor). The average volume-based particle diameter of the obtained microspheres was 29.8 Representative particles were frozen with liquid nitrogen, and an FIB cross section was prepared, and an SEM image (FIG. 10) was observed.

The observed SEM image was image analyzed in the same manner as in Examples 1 to 4. The variation coefficient of the area ratios: (s/A)×100 (%), wherein A is an area of a respective region obtained by dividing into six regions on the SEM image latitudinally every 60° around the center point of the maximum diameter as a center, and s is a sum of cross section areas of the biologically active substance included in the respective divided region, was 0.357.

Comparative Example 3

69.75% by mass of dichloromethane (Kanto Chemical Co., Inc.) and 25% by mass of acetone (Kanto Chemical Co., Inc.) were added to lactic acid-glycolic acid copolymer (Resomer RG504, Evonik AG) and curcumin (FUJIFILM Wako Pure Chemical Corporation, Wako special grade) as a biologically active substance, so that the concentration of lactic acid-glycolic acid copolymer was 5.0% by mass, and the concentration of curcumin was 0.25% by mass. Lactic acid-glycolic acid copolymer and curcumin were dissolved using a high-speed rotatory dispersing apparatus Clearmix Dissolver (M. Technique Co., Ltd.) to obtain a solution of PLGA and the biologically active substance. Thereafter, the solution was filtrated with a 0.2 μm air vent filter (φ 62, Merck KGaA). An aqueous PVA solution was prepared in the same manner as in Reference Example 1. The aqueous PVA solution was added in a tank for collecting emulsified particles of PLGA and the biologically active substance beforehand, and was slowly stirred to an extent that the solution surface just moved.

Figure 11:
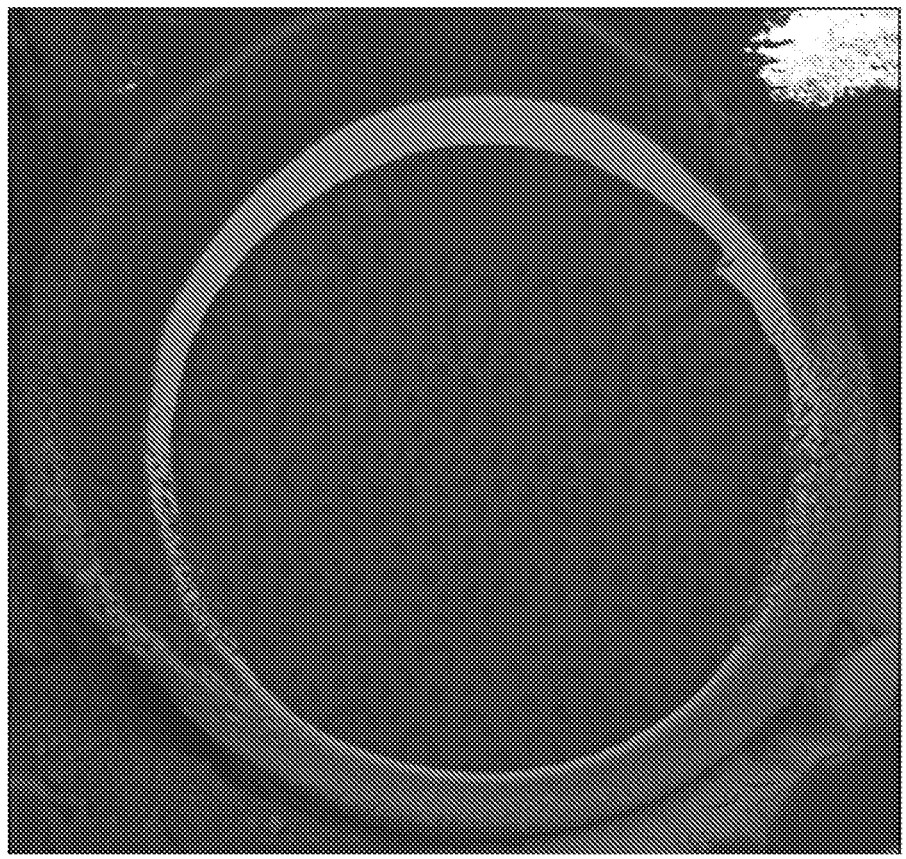
FIG. 11 shows an SEM image of a cross section of the microsphere of Comparative Example 3.

The step of forming particles and the step of removing a solvent were performed to obtain a dispersion containing microspheres in the same manner as in Example 1. The average volume-based particle diameter of the obtained microspheres was 6.8 Representative particles were frozen with liquid nitrogen, and an FIB cross section was prepared, and an SEM image (FIG. 11) was observed.

The observed SEM image was image analyzed in the same manner as in Examples 1 to 4. The variation coefficient of the area ratios: (s/A)×100 (%), wherein A is an area of a respective region obtained by dividing into six regions on the SEM image latitudinally every 60° around the center point of the maximum diameter as a center, and s is a sum of cross section areas of the biologically active substance included in the respective divided region, was 0.386.

Comparative Example 4

69.5% by mass of dichloromethane (Kanto Chemical Co., Inc.) and 25% by mass of acetone (Kanto Chemical Co., Inc.) were added to lactic acid-glycolic acid copolymer (Resomer RG504, Evonik AG) and progesterone (Sigma-Aldrich Co., LLC) as a biologically active substance, so that the concentration of lactic acid-glycolic acid copolymer was 5.0% by mass, and the concentration of curcumin was 0.3% by mass. Lactic acid-glycolic acid copolymer and progesterone were dissolved using a high-speed rotatory dispersing apparatus Clearmix Dissolver (M. Technique Co., Ltd.) to obtain a solution of PLGA and the biologically active substance. Thereafter, the solution was filtrated with a 0.2 µm air vent filter (φ 62, Merck KGaA). An aqueous PVA solution was prepared in the same manner as in Reference Example 1. The aqueous PVA solution was added in a tank for collecting emulsified particles of PLGA and the biologically active substance beforehand, and was slowly stirred to an extent that the solution surface just moved.

Figure 12:
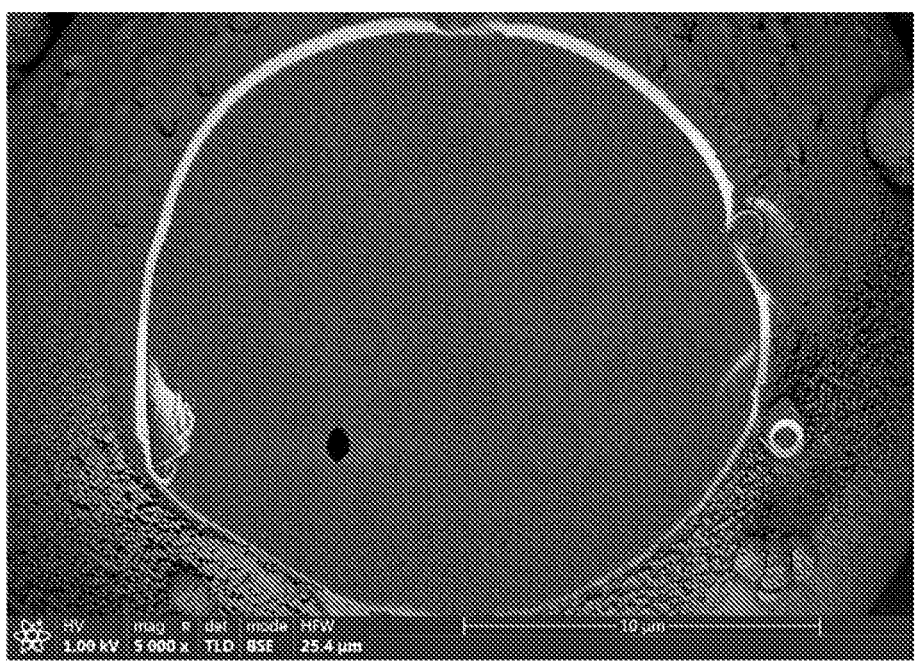
FIG. 12 shows an SEM image of a cross section of the microsphere of Comparative Example 4.

The step of forming particles and the step of removing a solvent were performed to obtain a dispersion containing microspheres in the same manner as in Example 3. The average volume-based particle diameter of the obtained microspheres was 21.6 µm. Representative particles were frozen with liquid nitrogen, and an FIB cross section was prepared, and an SEM image (FIG. 12) was observed.

The observed SEM image was image analyzed in the same manner as in Examples 1 to 4. The variation coefficient of the area ratios: $(s/A) \times 100$ (%), wherein A is an area of a respective region obtained by dividing into six regions on the SEM image latitudinally every 60° around the center point of the maximum diameter as a center, and s is a sum of cross section areas of the biologically active substance included in the respective divided region, was 1.094.

A part of the conditions of Examples 1 to 4, Comparative Examples 1 to 4, and Reference Example 1 (containing only PLGA) is shown in Table 1.

TABLE 1

|  | Example 1 | Example 2 | Example 3 | Example 4 | Comparative Example 1 | Comparative Example 2 | Comparative Example 3 | Comparative Example 4 | Reference Example 1 |
|---|---|---|---|---|---|---|---|---|---|
| Medicine | Curcumin | Curcumin | Progesterone | Probucol | Probucol | Probucol | Curcumin | Progesterone | — |
| Concentration of medicine | 0.5% by mass | 0.5% by mass | 1% by mass | 1% by mass | 1% by mass | 1% by mass | 0.25% by mass | 0.3% by mass | — |
| PLGA or PLA | PLGA (RG752H) | PLA (R202H) | PLGA (RG504) | PLGA (RG504) | PLGA (RG504) | PLGA (RG504) | PLGA (RG504) | PLGA (RG504) | PLGA (RG504) |
| Concentration of PLGA or PLA | 10% by mass | 10% by mass | 13% by mass | 13% by mass | 13% by mass | 13% by mass | 5% by mass | 5% by mass | 13% by mass |
| Drying condition | Argon flow 3.5 hours | Argon flow 3.5 hours | Argon flow 3.5 hours | Argon flow 3.5 hours | In atmosphere 42 hours | Argon flow 3.5 hours | Argon flow 3.5 hours | Argon flow 3.5 hours | Argon flow 3.5 hours |
| Preparation condition of solution of PLGA or PLA and biologically acitve substance | High speed stirring | High speed stirring | High speed stirring | High speed stirring | High speed stirring | Propeller | High speed stirring | High speed stirring | High speed stirring |
| Particle diameter of microsphere | 7.5 µm | 7.3 µm | 34.8 µm | 32.5 µm | 31.8 µm | 29.8 µm | 6.8 µm | 21.6 µm | 34.0 µm |

Area ratios (%) in respective regions, standard deviations, averages and variation coefficients (CV values) of a microsphere having a representative particle diameter of Examples 1 to 4, Comparative Examples 1 to 4, and lueplin are shown in Table 2.

TABLE 2

|  | Area ratio (%) | | | | | | Standard deviation | Average | CV value |
|---|---|---|---|---|---|---|---|---|---|
|  | Region 1 | Region 2 | Region 3 | Region 4 | Region 5 | Region 6 | | | |
| Example 1 | 43.28 | 46.53 | 41.96 | 35.68 | 31.60 | 32.38 | 6.20 | 38.57 | 0.161 |
| Example 2 | 31.32 | 32.63 | 46.82 | 30.11 | 48.15 | 35.66 | 8.00 | 37.45 | 0.214 |
| Example 3 | 34.68 | 35.51 | 38.12 | 33.93 | 35.11 | 38.99 | 2.02 | 36.06 | 0.056 |
| Example 4 | 28.64 | 30.56 | 36.89 | 17.29 | 33.46 | 35.86 | 7.16 | 30.45 | 0.235 |
| Comparative Example 1 | 14.28 | 21.68 | 4.62 | 23.56 | 22.13 | 31.56 | 9.19 | 19.64 | 0.468 |
| Comparative Example 2 | 32.79 | 15.62 | 13.18 | 34.92 | 31.55 | 28.91 | 9.35 | 26.16 | 0.357 |
| Comparative Example 3 | 25.62 | 8.65 | 14.53 | 21.88 | 29.54 | 28.23 | 8.25 | 21.41 | 0.386 |
| Comparative Example 4 | 2.38 | 3.50 | 23.62 | 21.55 | 3.12 | 2.12 | 10.26 | 9.38 | 1.094 |
| Leuplin | 22.02 | 25.12 | 5.37 | 3.40 | 1.31 | 2.80 | 10.64 | 10.00 | 1.063 |

As can be seen from Tables 1 and 2, in Examples 1 and 2, the variation coefficients of area ratios of occupation of the biologically active substance in respective regions in the particles, were 0.35 or less, and the biologically active substance was uniformly dispersed in the particles, even when either of PLGA or PLA was used. In Comparative Example 3, when the concentration of PLGA was decreased, uniformity in the particles was lowered, and the variation coefficients of area ratios of occupation of the biologically active substance in respective regions, became bigger to 0.386, even when conditions in the step of forming particles and the step of removing a solvent were the same as those in Example 1.

In Example 4 and Comparative Example 1, the particle diameter of the microparticles of the biologically active substance varied according to difference of the drying conditions and drying time. In Comparative Example 1 in which the drying time was long, uniformity of the biologically active substance dispersed in the particles was lowered, and the variation coefficient of area ratios of occupation of the biologically active substance in respective regions, became bigger to 0.468. In Comparative Examples 3 and 4 in which the concentrations of PLGA and the medicine were decreased compared with those in Examples, percentage of contraction during drying became bigger, and the biologically active substance was biased in the particles, and the variation coefficients of area ratios of occupation of the biologically active substance in respective regions, exceeded 0.35.

INDUSTRIAL APPLICABILITY

The present invention provides a microsphere capable of appropriately controlling the initial release amount of a biologically active substance and its release rate during a subsequent release period, and continuously releasing the biologically active substance in vivo for a predetermined period of time.

The invention claimed is:
1. A method of producing a microsphere comprising a lactic acid-glycolic acid copolymer (PLGA) or polylactide (PLA) as a main component, in which a biologically active substance is uniformly dispersed, comprising:
   a step of continuously feeding to a pulverizing apparatus a solution of the PLGA or PLA and the biologically active substance obtained by dissolving or dispersing the PLGA or PLA and the biologically active substance in a good solvent of PLGA or PLA, and a solution containing a poor solvent of PLGA or PLA to prepare emulsified particles; and removing the good solvent from the prepared emulsified particles to precipitate the microsphere;
   wherein the good solvent is a solvent which dissolves 0.1 g or more of PLGA or PLA in 100 g of the solvent at 25° C., and the poor solvent is a solvent which dissolves only 0.05 g or less of PLGA or PLA in 100 g of the solvent at 25° C.,
   an average volume-based particle diameter of the microsphere is 1 μm or more and 150 μm or less, and
   a variation coefficient of area ratios of an area of the biologically active substance to a cross-section area of the microsphere in six regions of the microsphere is 0.35 or less.
2. The method according to claim 1, wherein the biologically active substance is a lipophilic biologically active substance.
3. The method according to claim 1, wherein an average volume-based particle diameter of the dispersed biologically active substance is 5 nm to 500 nm.
4. The method according to claim 1, wherein a content of the biologically active substance in the microsphere is 0.35 to 1.5% by mass.
5. The method according to claim 1, wherein the good solvent is removed by blowing a gas on a surface of a fluid containing the emulsified particles, while stirring the fluid.

* * * * *